United States Patent [19]

Wynberg et al.

[11] Patent Number: 4,973,756
[45] Date of Patent: Nov. 27, 1990

[54] HYDROXYLATED ENE KETONES, ACETYLENIC GRIGNARDS AND HYDROXYLATED YNE KETONES THEREFROM

[75] Inventors: Hans Wynberg, Groningen; Wolter T. Hoeve, Eelde; Gerrit A. Barf, Groningen; Johannes N. Koek, Sauwerd, all of Netherlands; David R. Borcherding, Roeland Park, Kans.

[73] Assignee: Marion Laboratories, Inc., Kansas City, Mo.

[21] Appl. No.: 395,933

[22] Filed: Aug. 21, 1989

[51] Int. Cl.$^5$ ................. C07C 221/00; C07C 223/00; C07C 225/00

[52] U.S. Cl. ................................. 564/343; 544/175; 544/358; 544/387; 546/190; 548/571; 564/344; 568/310; 568/312; 568/315; 568/316; 568/317; 568/318

[58] Field of Search ............................... 564/343, 344

[56] References Cited

PUBLICATIONS

Roberts et al., *Basic Principles of Organic Chemistry*, California Institute of Technology, 1964, pp. 356–358.
Hansen et al., *J. Am. Chem. Soc.*, 100, pp. 2244–2245, (1978), "Nickel–Catalyzed Conjugate Addition of Organoaluminum acetylides to $\alpha,\beta$–Enones".
Sinclair et al., *J. Am. Chem. Soc.*, 99, (1977), "Conjugate Addition of $\beta$-1-Alkynyl-9-borabicyclononanes to $\alpha,\beta$–Unsaturated Ketones, A Convenient Systhesis of $\gamma,\delta$–Acetylenic Ketones", pp. 954–956.
Corey et al., *J. Am. Chem. Soc.*, 96, pp. 5581–5583, (1974), "A Nucleophilic Ethynyl Group Equivalent and Its Use in Conjugate Addition to $\alpha,\beta$–Enones".
Hoff et al., *Rec. Trav. Chim.*, 87, pp. 916–924, (1968), "Preparation, Metallation and Alkylation of Allenyl Ethers".
Keana et al., *J. Org. Chem.*, 47, pp. 347–352, (1982), "Synthesis of Diamagnetic Structural Analogues of Representative Doxyl, Proxyl, Piperidine, and Pyrroline Nitroxide Spin Labels".
Brandsma, *Preparative Acetylenic Chemistry*, 2nd Ed., Elsevier, (1988), pp. 259–260, "Methyl Propargyl Alcohol, Dimethyl Sulfate and NaOH".
Hoff et al., *Rec. Trav. Chim*, 87, pp. 1179–1184, (1968), "Some Conversions of Allenyl Ethers".
Verkruijsse et al., *Rec. Trav. Chim.*, 100, pp. 244–246, (1981), "Base–Catalysed Isomerization of 2-Propynylamines, Synthesis of (dialkylamino)allenes".
Bruhn et al., *Tetrahydron Lett.*, No. 4, pp. 235–238, (1976), Pergamon Press, "Synthesis and Properties of 16-Hydroxy Analogs of PGE$_2$".

*Primary Examiner*—Glennon H. Hollrah
*Assistant Examiner*—Scott C. Rand
*Attorney, Agent, or Firm*—Christopher J. Rudy

[57] ABSTRACT

An alpha-hydroxyl-alpha,alpha-di(inert-substituted)-gamma',delta'-yne ketone can be prepared by a procedure comprising contacting an acetylenic Grignard reagent with an alpha-hydroxyl-alpha,alpha-di(inert substituted)-alpha',beta'-ene ketone, and the alpha-hydroxyl-alpha,alpha-di(inert-substituted)-alpha',beta'-ene ketone can be prepared by a procedure comprising steps of contacting, first, an alkoxy allene with a lithium donating organic agent, second, product of the first step with a di(inert-substituted)ketone, and third, product of the second step with an acidic substance. For example, 1-cyclobutyl-7-(N,N-dimethylamino)-1-hydroxy-1-phenylhept-5-yn-2-one, hydrochloride salt (ML-1012), can be prepared by the reaction of 1-cyclobutyl-1-hydroxy-1-phenylbut-3-en-2-one and 1-(N,N-dimethylamino)-2-propyn-3-magnesium chloride, followed by salt formation with hydrogen chloride gas, and the 1-cyclobutyl-1-hydroxy-1-phenylbut-3-en-2-one can be prepared by the serial reactions of (1) 1-methoxy allene with n-butyllithium, (2) product of this first step with cyclobutylphenyl ketone, and (3) product of this second step with sulfuric acid.

11 Claims, No Drawings

HYDROXYLATED ENE KETONES, ACETYLENIC GRIGNARDS AND HYDROXYLATED YNE KETONES THEREFROM

FIELD

This invention concerns procedures for preparing organic compounds, and said compounds as well. The organic compounds are useful chemicals including pharmaceuticals.

BACKGROUND

Rzeszotarski et al., Eur. Pat. Appl. No. 0 251 126 published on Jan. 7, 1988, discloses 1,7-substituted heptyne-2-ones. The compounds of that invention can be prepared by reaction of an appropriate dithiane and ketone followed by removal of a dithiane protective group. See, the examples thereof for their preparation, and also, Example V for another preparation involving propargylation and Mannich condensation.

Rzeszotarski et al., U.S. patent application Ser. No. 07/155,110 filed on Feb. 11, 1988, discloses 1,7-substituted heptyn-2-ones and methods for their manufacture. These heptyn-2-ones can be prepared according to the practice of that invention by a variety of synthetic routes. One of these sequences involves Mannich condensation of pent-4-yn-1-ol with formaldehyde and the appropriate amine followed by sequential oxidation of the alcohol to an aldehyde, conversion of the aldehyde to a dithiane, condensation of the dithiane with an appropriate aryl ketone and lastly dithiane deprotection to the 1,7-substituted hept-5-yn-2-one. Another method involves addition of lithium acetylide to the aryl ketone, oxidation of the resulting acetylide to a methyl ketone which is sequentially propargylated to give an acetylenic derivative which is subjected to appropriate Mannich condensation. Alternatively, the methyl ketone can be alkylated with 1,4-dibromo-2-butyne to give a bromo derivative that can be alkylated to provide the product. In another route, the aryl ketone can be condensed with 1-(diethoxyphosphinyl)-1-trimetylsilyloxy ethane to give a methyl ketone that is propargylated and aminomethylated to give the product. Another sequence begins with an appropriate disubstituted glycolic acid which is converted to the methyl ketone that is transformed to product via the aforementioned propargylation, Mannich condensation sequence. According to another method, a 1-dialkoxyphosphinyl-1-trialkylsilyloxyethane having one to four carbons in one each of the alkyl and alkoxy groups is condensed with a ketone of the formula R'C(=O)R in which R has the meaning set forth in the general formula (IV) as described hereinafter, and R' is a phenyl or para-fluorophenyl group; the resulting 1,1-disubstituted-1-trialkylsilyloxy-2-propanone is propargylated followed by Mannich reaction of the product with formaldehyde and ammonia or an appropriate amine, which have the formula HNR" in which R" has the meanings set forth in the general formula (IV) as described hereinafter, and the silyl protecting group is thereafter removed. Yet another route for synthesizing the compounds involves ethynylation of a ketone to give a 1,1-disubstituted-1-hydroxypropyne which is oxidized to the corresponding 1,1-disubstituted-1-hydroxy propanone, which was alkylated with 1,4-dibromobutyne to yield 1,1-disubstituted-1-hydroxy-7-bromohept-5-yn-2-one, which is aminated to give the final compound.

Hansen et al., J. Am. Chem. Soc., 100, 2244 (1978), reports on nickel-catalyzed conjugate addition of organoaluminum acetylides to alpha, beta-enones.

Bruhn et al., Tetrahedron Lett., 235 (1976), reports on synthesis and properties of 16-hydroxy analogs of PGE2.

Sinclair et al., J. Am. Chem. Soc., 99, 954 (1977), reports on conjugate addition of B-1-alkynyl-9-borabicyclo[3.3.1]nonanes to alpha, beta-unsaturated ketones, a convenient synthesis of gamma, delta-acetylenic ketones.

Corey et al., J. Am. Chem. Soc., 96, 5581 (1974), reports on a nucleophilic ethynyl group equivalent and its use in conjugate addition to alpha, beta-enones.

Hoff et al., Rec. Trav. Chim., 87, 1179 (1968), reports on some conversions of allenyl ethers.

Keana et al., J. Org. Chem., 47, 347 (1982), reports on synthesis of diamagnetic structural analogues of representative doxyl, prolyl, piperidine, and pyrroline nitroxide spin labels. At page 348, a vinyl ketone (16) was reported to have resulted from a hydrolysis reaction.

Brandsma, "Preparative Acetylenic Chemistry, 2nd Ed.," Elsevier, 259 (1988), reports on methyl propargyl ether from propargyl alcohol, dimethyl sulfate and sodium hydroxide.

Hoff et al., Rec. Trav. Chim., 87, 916 (1968), reports on preparation, metallation and alkylation of allenyl ethers, to include methods related to reactions of allenes with butyllithium to prepare lithiated allenyl ethers.

Verkruijsse et al., Rec. Trav. Chim., 100, 244 (1981), reports on base-catalyzed isomerization of 2-propynylamines, synthesis of (dialkylamino)allenes, and preparation of 2-propynylamines.

What is lacking and what is needed in the art are solutions to problems presented. In particular, yields and purities of 1,7-substituted heptyn-2-ones would desirably be improved. Furthermore, improvements therein might find more widespread application in more generalized fields.

SUMMARY

The present invention provides, in first aspects, a procedure for preparing an alpha-hydroxyl-alpha,alpha-di(inert-substituted)-gamma',delta'-yne ketone comprising contacting an acetylenic Grignard reagent with an alpha-hydroxyl-alpha,alpha-di(inert substituted)-alpha',beta'-ene ketone by step(s) under conditions sufficient to prepare said yne ketone. Said yne ketone includes a 1,1-di(inert-substituted)-1-hydroxyl-7-Aminohept-5-yn-2-one, or salt(s) thereof. Another aspect is a procedure for preparing an alpha-hydroxyl-alpha,alpha-di(inert-substituted)-alpha',beta'-ene ketone comprising steps of contacting, first, an alkoxy allene with a lithium donating organic agent, second, product of the first step with a di(inert-substituted)ketone, and third, product of the second step with an acidic substance, under conditions sufficient to prepare said ene ketone.

The present invention is useful for preparing organic compounds. These compounds can generally have utility as pharmaceuticals, for example, as selective muscarinic acetylcholine receptor antagonists having particular activity in the treatment of neurogenic bladder disorder, especially as concerns the 1,1-di(inert-substituted)-1-hydroxy-7-Aminohept-5-yn-2-ones, or salt(s) thereof, or as intermediates thereto.

Significantly, the procedural aspects of this invention can provide highly pure products in good to excellent yields, thus being highly efficient. The provision of an essentially pure 1,1-di(inert-substituted)-1-hydroxy-7-Aminohept-5-yn-2-one, or salt(s) thereof, is a notable advance in the art, which can be prepared efficiently by the practice of this invention, thus overcoming a significant problem in the art. Moreover, the employment of the acetylenic Grignard reagent in preparing the alpha-hydroxyl-alpha,alpha-di(inert-substituted)-gamma',delta'-yne ketone from the alpha-hydroxyl-alpha,alpha-di(inert-substituted)-alpha',beta'-ene ketone, is a most spectacular advance in the art because (1) said ene ketone, a free hydroxylated carbonyl compound, can be added to by the Grignard reagent away from the hydroxyl moiety but even more notably away from the carbonyl moiety, and (2) additional complexing agents such as copper compounds and so forth, as otherwise known to be required in the art, are not required in the practice of this invention.

Further advantages attend this invention as well.

ILLUSTRATIVE DETAIL

Herein, a procedure is a method and/or process.

The term "alpha-hydroxyl-alpha,alpha-di(inert-substituted)-gamma',delta'-yne ketone" refers herein to a ketone which, in addition to the carbonyl carbon of the ketone that may be considered to be substituted on one carbon alpha to this carbonyl carbon, is further substituted by three groups on this one carbon alpha to the carbonyl carbon featured in the ketone, and is also acetylenically unsaturated between carbons delta and gamma to this same carbonyl carbon, with these delta and gamma carbons residing on the opposite side of the same carbonyl carbon from the mentioned alpha carbon. Hence, the prime (') notations appear on these gamma and delta positions, thus: "gamma' and delta'." The mentioned alpha carbon bears, in general, one hydroxyl and two inert-substituted groups.

The term "inert-substituted" refers herein to substituted groups or moieties which do not generally interfere with the appropriate reaction during the procedural practice of this invention. Representative examples of inert-substituted groups or moieties include such organic groups as, for instance, aromatics to include phenyl, alkyl- and/or halogen-substituted phenyl, naphthyl, phenyl-, alkyl- and/or halogen-substituted naphthyl, and so forth, saturated organics to include alkyl, which includes cycloalkyl, for example, methyl, ethyl, propyl to include cyclopropyl, butyl to include cyclobutyl and methyl-substituted cyclopropyl, pentyl to include, e.g., cyclopentyl and methyl-substituted cyclobutyl, hexyl to include, e.g., cyclohexyl, methyl-substituted cyclopentyl and di-methyl or ethyl-substituted cyclobutyl, heptyl to include cycloheptyl, etc., octyl to include cyclooctyl, etc., halogen-substituted alkyl to include halogen-substituted chloroalkyl, e.g., fluoroalkyl, chloralkyl, and so forth and the like.

The inert-substituted group may be considered to be sterically hindering, particularly in regard to procedures with the alpha-hydroxyl-alpha, alpha-di(inert-substituted)-alpha',beta'-ene ketone. The term "sterically hindering" especially refers herein to groups which in general may hinder access about the mentioned alpha-carbon, to which is associated the noted hydroxyl and carbonyl groups, in the alpha-hydroxyl-alpha,alpha-di(inert-substituted)-alpha',beta'-ene ketone.

The term "generally inert" refers herein to such moieties as the inert-substituted groups and moieties, to include tertiary amino groups, and further refers herein to such a moiety as hydrogen.

Accordingly, the alpha-hydroxyl-alpha,alpha-di(inert-substituted)-gamma',delta'-yne ketone can be a compound represented by the following general formula:

$$Q_2(OH)C-C(=O)-CH_2-CHQ'-C\equiv C-Q'' \qquad (I)$$

wherein

Q is independently at each occurrence an inert-substituted group;

Q' is a generally inert moiety, preferably H, and

Q" is a generally inert moiety, preferably containing a tertiary amino group.

The term "acetylenic Grignard reagent" refers herein to a compound which can be represented by the following general formula:

$$Q''-C\equiv C-MgX \qquad (II)$$

wherein

Q" is as set forth in the formula (I), and

X is an appropriate halogen, preferably Cl.

Of note in connection with the acetylenic Grignard reagent, Q" is preferably $CH_2-NR''_2$ as set forth in the formula (IV), and when this represents a primary or secondary amino group on such compounds as those represented by the formulae (I) & (IV), such primary and secondary amino groups, incipient on the acetylenic Grignard reagent, are protected on the acetylenic Grignard reagent. Protection of these amino groups can be accomplished by methods known in the art such as, for example, amidation with a suitable carboxylic acid such as, for example, acetic acid, and so forth, to form N-carboxyl, e.g., N-acetyl, and so forth, derivatives. In effect, in the practice of this invention, the acetylenic Grignard reagent itself has no active hydrogens available on it, and in the instance of the protected primary and secondary amino groups, these latter groups may be considered as tertiary amino groups for the time of reaction with the acetylenic Grignard reagent. Subsequent deprotection of these groups can be accomplished by methods known in the art such as, for example, hydrolysis with a suitable acid. The deprotection can be carried out following initial preparation of the aforesaid yne ketone and can leave the primary or secondary amino groups or other appropriate groups having active hydrogen in such compounds as represented by those of the formulae (I) and (IV).

The term "alpha-hydroxyl-alpha,alpha-di(inert-substituted)-alpha',beta'-ene ketone" refers herein to a ketone which, in addition to the carbonyl carbon of this ketone that may be considered to be substituted on one carbon alpha to this carbonyl carbon, is further substituted by three groups on this one carbon alpha to the carbonyl carbon featured in the ketone, and is also ethylenically unsaturated between carbons alpha and beta to this same carbonyl carbon, with these latter-mentioned alpha and beta carbons residing on the opposite side of the same carbonyl carbon from the first-mentioned alpha carbon. Hence, the prime (') notations appear on these latter-mentioned alpha and beta positions, thus: "alpha' and beta'." The first-mentioned alpha carbon bears, in general, one hydroxyl and two inert-substituted groups.

Accordingly, the alpha-hydroxyl-alpha,alpha-di(inert-substituted)-alpha',beta'-ene ketone can be a compound represented by the following general formula:

$$Q_2(OH)C-C(=O)-CH=CHQ' \quad (III)$$

wherein Q and Q' are each as in the formula (I).

The term "1,1-di(inert-substituted)-1-hydroxy-7-Aminohept-5-yn-2-one" refers herein to a compound which can be represented by the following general formula:

$$RR'(HO)C-C(=O)-(CH_2)_2-C\equiv C-CH_2-NR''_2 \quad (IV)$$

wherein

R is inert-substituted alkyl having up to seven carbon atoms, cycloalkyl having three to six carbon atoms, polycycloalkyl of seven to eleven carbon atoms, or substituted or unsubstituted aryl, polycycloaryl, polycycloakyl, or heteroaryl;

R' is phenyl or para-fluorophenyl, and

R" is independently at each occurrence hydrogen, alkyl having one to three carbon atoms, or phenylalkyl with its alkyl moiety having one to three carbon atoms, or R"$_2$ is tetramethylene, pentamethylene, or hexamethylene. As such, these compounds are a specific set of the alpha-hydroxyl-alpha,alpha-di(inert-substituted)-gamma',delta'-yne ketones, with the R and R' replacing each Q, with H replacing each Q', and with CH$_2$—NR"$_2$ replacing Q", as from the compounds of the formula (I).

In compounds of the formula (IV) the cycloalkyl groups have one alkyl ring as in cyclopropyl, cyclobutyl and cyclohexyl, and the polycycloalkyl groups have more than one alkyl ring as in adamantyl, bornyl, caranyl, norbornyl, norcaranyl, pinanyl, thujanyl, and so forth. The aryl groups have one aromatic carbon ring as in phenyl, toluyl, and so forth, and the polycycloaryl groups have more than one carbon ring, at least one of which is an aromatic carbon ring, as in biphenyl, naphthyl, tetrahydronaphthyl, and so forth. Among heterocyclic moieties suitably employed in compounds of the formula (IV) are included such heteroaryls as pyridyl, including both 3-pyridyl and 4-pyridyl, and such heterocycloalkyls as those having five- or six-membered fully saturated rings having one nitrogen or having two nitrogens opposite one another with such ring being bonded to the number one carbon in compounds of the formula (IV) through a methylene group bonded to one of the nitrogens or to a saturated carbon opposite the single nitrogen of such a six-membered ring. Substituents for the substituted aryl and polycycloaryl groups include halogen, preferably fluoro, hydroxy, nitro, methoxy, methyl, trifluoromethyl, acetyl, and amino, and substituents for the substituted heteroaryl or substituted heterocycloalkyl groups may be selected from among those permitted as aryl substituents. Where the heterocyclic compound is substituted, the substituent is preferably bonded to a nitrogen atom and preferably is a methyl or an acetyl group. In particular, preferred saturated heterocyclic NR"$_2$ substituents include those which can be represented by the following formulae:

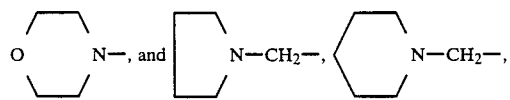

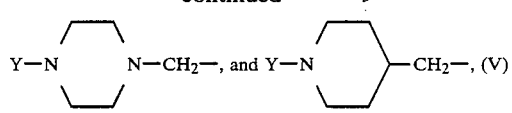

with Y being selected from alkyl groups of one to three carbon(s), acetyl, or phenylethyl. Nonetheless, in compounds of the formula (IV), R is preferably aryl, cycloalkyl or polycycloalkyl, and most preferably is a phenyl group, cyclobutyl group, a cyclohexyl group, or an adamantyl group, but especially cyclobutyl. When R is a phenyl group, it is preferably a para-substituted phenyl group, most preferably substituted by a fluoro moiety. In compounds of the formula (IV), each R" group is independently hydrogen, an alkyl group of one to three carbon(s), particularly methyl or ethyl, a phenylalkyl group such as, for example, phenylethyl, or both R" groups together with the nitrogen form a heterocyclo group having four to six carbons.

Compounds of the formula (IV), for example, may be present as substantially pure or optically enriched d- or l-optical isomers as well as being present in racemic mixtures. Further, some of the compounds in which R is a substituted cycloalkyl or a polycycloalkyl group may be present as enantiomers which may be resolved into optical isomers. Resolution of enantiomers may be accomplished by fractional crystallization of their diastereomeric salts with such optically active acids such as, for example, tartaric, camphor-10-sulfonic, 0,0,-dibenzoyltartaric, 0,0-di(p-toluyl)tartaric, menthyloxyacetic, camphoric, or 2-pyrrolidone-5-carboxylic acids or N-acetyltryptophane, and so forth, from appropriate solvents. They may also be prepared by stereoselective synthesis or by chromatographic techniques using chiral substrates or derivatives. Unless otherwise specified herein, the present invention includes all isomers to include stereoisomers, whether isolated or in mixtures thereof.

Preferred compounds of the formula (IV) include those in which R is phenyl, cyclohexyl, cyclopropyl, cyclobutyl, cyclopentyl, or polycloalkyl, and R" is independently at each occurrence hydrogen, methyl or ethyl. Preferred compounds thus include 1-cyclohexyl-1-phenyl-1-hydroxy-7-dimethylaminohept-5-yn-2-one; 1-cyclohexyl-1-phenyl-1-hydroxy-7-methylaminohept-5-yn-1-one; 1-cyclohexyl-1-phenyl-1-hydroxy-7-ethylaminohept-5-yn-2-one; 1-cyclobutyl-1-hydroxy-1-phenyl-7-dimethylaminohept-5-yn-2-one, and 1-bicyclo[2.2.1]hept-2-yl-1-hydroxy-1-phenyl-7-dimethylaminohept-5-yn-2-one. Compounds of the formula (IV) also include: 2-hydroxy-2-phenyl-8-(N,N-diethylamino)oct-6-yn-3-one; 1-cyclohexyl-1-hydroxy-1-phenyl-7-diisopropylaminohept-5-yn-2-one; 1-cyclohexyl-1-hydroxy-1-phenyl-7-(N-methyl-N-ethylamino)hept-5-yn-2-one; 1-cyclohexyl-1-hydroxy-1-phenyl-7-isopropylaminohept-5-yn-2-one; 1-cyclohexyl-1-phenyl-7-(N-methyl-N-isopropylamino)-hept-5-yn-2-one; 1-cyclohexyl-1-hydroxy-1-phenyl-7-t-butylaminohept-5-yn-2-one; 1-cyclohexyl-1-hydroxy-1-phenyl-7-(N-ethyl-N-isopropylamino)hept-5-yn-2-one; 1-cyclohexyl-1-hydroxy-1-phenyl-7-(N-methyl-N-phenethylamino)-hept-5-yn-2-one; 1-cyclohexyl-1-hydroxy-1-phenyl-7-pyrrolidinylhept-5-yn-2-one; 1-(6-N,N-diethylamino)hex-4-yn-2-one)-1-hydroxyindan; 1-cyclohexyl-1-hydroxy-1-phenyl-7-(N-methyl-N-benzylamino)hept-5-yn-2-one; 1-cyclopentyl-1-hydroxy-1- phenyl-7-(N-methyl-N-ethylamino)hept-5-yn-2-one; 1-cyclopropyl-1-hydroxy-1-phenyl-7-diethylaminohept-5-yn-2-one; 1-cyclohexyl-1-hydroxy-1-phenyl-7-aminohept-5-yn-2-one; 1-cyclohexyl-1-hydroxy-1-phenyl-7-di-n-butylaminohept-5-yn-2-one; 1-cyclopentyl-1-hydroxy-1-phenyl-7-dimethylaminohept-5-yn-2-one; 1-cyclopropyl-1-hydroxy-1-phenyl-7-(N-methyl-N-ethylamino)hept-5-yn-2-one; 1-cyclohexyl-1-hydroxy-1-phenyl-7-di-n-propylaminohept-5-yn-2-one; 1,1-diphenyl-1-hydroxy-7-ethylaminohept-5-yn-2-one; 1,1-diphenyl-1-hydroxy-7-(N-ethyl-N-methylamino)hept-5-yn-2-one; 1,1-diphenyl-1-hydroxy-7-dimethylaminohept-3-yn-2-one; 1-cyclopropyl-1-hydroxy-1-phenyl-7-ethylaminohept-5-yn-2-one; 1-cyclopropyl-1-hydroxy-1-phenyl-7-dimethylaminohept-5-yn-2-one; 1-cyclohexyl-1-hydroxy-3-methyl-1-phenyl-7-dimethylaminohept-5-yn-one; 1-(1-adamantyl)-1-hydroxy-1-phenyl-7-dimethylaminohept-5-yn-2-one; 1-cyclohexyl-1-hydroxy-1-(4-fluorophenyl)-7-dimethylaminohept-5-yn-2-one; 1-cyclohexyl-1-hydroxy-1-(4-fluorophenyl)-7-ethylaminohept-5-yn-2-one; (S)-1-cyclohexyl-1-hydroxy-1-phenyl-7-dimethylaminohept-5-yn-2-one; 1-cyclohexyl-1-hydroxy-1-phenyl-7-[N-(2-hydroxyethyl)-N-methyalmino]hept-5-yn-2-one; 1-bicyclo[2.2.1]hept-2-yl-hydroxy-1-phenyl-7-ethylaminohept-5-yn-2-one; (R)-1-cyclohexyl-1-hydroxy-1-phenyl-7-dimethylaminohept-5-yn-one; 1-cyclobutyl-1-hydroxy-1-phenyl-7-(N-ethyl-N-methylamino)hept-5-yn-2-one; 3-hydroxy-2-methyl-3-phenyl-9-dimethylaminonon-7-yn-4-one; 1-(1-methyl-cyclopropyl)-1-hydroxy-1-phenyl-7-dimethylaminohept-5-yn-2-one, and 4-hydroxy-2-methyl-4-phenyl-10-dimethylaminodec-8-yn-5-one, and so forth. Particularly preferred compounds are 1-cyclohexyl-1-hydroxy-1-phenyl-7-dimethylaminohept-5-yn-2-one and 1-cyclobutyl-1-hydroxy-1-phenyl-7-dimethylaminohept-5-yn-2-one, especially the lattermost compound, particularly as carried to its hydrochloride salt (ML-1012).

Salts of the compounds of the formula (IV) include such acid salts as, for example, hydrochloride, sulfate, phosphate, nitrate, methanesulfonate and tartrate salts, and so forth. Other salts to include other pharmaceutically acceptable salts are also within the spirit of the practice of this invention, as are the various possible hydrates of each of the compounds. Nonetheless, the salt is advantageously a hydrochloride salt.

The term "alkoxy allene" refers herein to a compound which can be represented by the following general formula:

$$Q'_2-C=C=C(H)OA \qquad (VI)$$

wherein

Q' is independently at each occurrence a generally inert moiety, most preferably H at each occurrence, and A is alkyl, most preferably methyl.

The term "lithium-donating organic agent" refers herein to an organic compound which is generally capable of exchanging a hydrogen with lithium on the same unsaturated carbon that bears the ether functionality of the alkoxy allene. However, the lithium substituted intermediate resulting from such an exchange need not be stable for appreciable periods or be isolatable, but it may be formed in situ or be part of a transitional intermediate, which may even be only theoretically present. Examples of lithium-donating organic compounds include n-butyllithium, sec-butyllithium and tert-butyllithium, and so forth.

The term "di(inert-substituted)ketone" refers herein to a ketone which is substituted on its carbonyl carbon independently at each occurrence by two inert-substituted groups. These inert-substituted groups may be not sterically hindering in connection with the practice of this invention with the di(inert-substituted)ketone.

Accordingly, the di(inert-substituted)ketone can be a compound represented by the following general formula:

$$Q_2C=O \qquad (VII)$$

wherein Q is as generally in the formula (I), noting the above as well.

The term "acidic substance" refers herein to a source of acidic hydrogen. The acidic substance is typically provided by the addition of a suitable acid to an aqueous liquid. The aqueous mixture containing the suitable acidic substance may generally contain other components such as an alcohol, for example, methanol, ethanol, propanols, phenol, and so forth. The suitable acid generally will not add across a double bond of an allene. Representative examples of such suitable acids in general include sulfuric acid, para-toluenesulfonic acid, acetic acid, trichloroacetic acid, and so forth and the like.

In general, in the practice of this invention in its first-noted aspects, the acetylenic Grignard reagent is contacted with the alpha-hydroxyl-alpha,alpha-di(inert-substituted)-alpha',beta'-ene ketone. Step(s) and conditions are those sufficient to prepare the alpha-hydroxyl-alpha,alpha-di(inert-substituted)-gamma',delta'-yne ketone, which includes the 1,1-di(inert-substituted)-1-hydroxyl-7-Aminohept-5-yn-2-one, or salt(s) thereof. No special conditions are generally required to effect preparation of said yne ketone with the acetylenic Grignard reagent and said ene ketone.

Typically however, this contact is carried out in a suitable diluent. The diluent may function as a solvent. Representative examples of suitable diluents generally include such substances as benzene, toluene, 1,4-dioxane, diethyl ether, tetrahydrofuran (THF), and so forth and the like.

Concentrations of the reactants in any diluent employed can generally vary over quite a broad range. As to the acetylenic Grignard reagent, concentrations about from 0.1 to 5 molar (M) are generally suitable for the contact. As to said ene ketone, concentrations about from 0.5 to 5M are generally suitable for the contact. Each reactant may be prediluted.

Temperatures for the contact can generally vary over quite a wide range but are typically moderate. Suitable temperatures thus generally include those about from 0 to 100 degrees C., with temperatures about from 50 to 70 degrees C. being advantageously employed.

Duration of the contact can generally vary over a fairly wide range. Suitable times generally include those about from several minutes to several hours.

The result of this contact in the practice of this invention is that said yne ketone is prepared. In the case of such yne ketones as the 1,1-di(inert-substituted)-1-hydroxy-7-Aminohept-5-yn-2-ones or others having such functionality as an appropriate amino group thereon, the yne ketone can be converted to an acid addition salt thereof by known methodology.

Yields of said yne ketone from said ene ketone can be quite good if not relatively excellent. In this connection, based on amounts of said ene ketone, presuming it is the limiting reagent, of course, yields of at least about 30 percent of theory, to at least about 40 percent of theory, to even at least about 50 percent of theory, can be achieved by the practice of this invention. Of course, if carrying the preparation of said yne ketone to corresponding salt, as may be appropriate, yields of said yne ketone as such a salt are, in general, diminished therefrom.

In general, the acetylenic Grignard reagent is prepared by contacting a terminal acetylene, which is a compound which can be represented by the following general formula:

$$Q''-C\equiv CH \tag{VIII}$$

wherein Q" is as defined in the formulae (I) and (IV), with an alkyl magnesium halide, which is a compound which can be represented by the following general formula:

$$A'MgX \tag{IX}$$

wherein

A' is a suitable alkyl group, for example, n-butyl, and
X is as defined in the formula (II).

This contact is typically carried out in a suitable diluent such as, for example, THF, and so forth. Temperatures of the contact can generally be about from 0 to 100 degrees C., with temperatures about from 50 to 70 degrees C. being preferred. The contact or reaction can be carried out for a suitable time, say, over the course of one to several hours, or so.

The alkyl magnesium halide can be provided by known methodology. Elemental iodine or the like may be added to initiate reaction in a suitable diluent, for example, THF, to form the alkyl magnesium halide from corresponding alkyl halide and magnesium metal, which can be provided as metal shavings or the like.

The acetylenic Grignard reagent can be used in situ.

In general, in the further practice of this invention, the alpha-hydroxyl-alpha,alpha-di(inert-substituted)-alpha',beta'-ene ketone is prepared by the following steps, conditions being those sufficient to prepare said ene ketone:

First, the alkoxy allene is contacted with the lithium donating organic agent.

Second, product of the first step is contacted with the di(inert-substituted)ketone.

Third, product of the second step is contacted with a suitable acidic substance such as provided in aqueous mixtures to hydrolyze the allene under acidic conditions which do not polymerize or destroy the characteristics of the alpha-hydroxyl-alpha,alpha-di(inert-substituted)-alpha',beta'-ene ketone.

The contact of the alkoxy allene with the lithium donating organic agent is generally done at a LOW temperature. The term "LOW temperature" herein refers to a temperature at which this step can be successfully carried out to any useful degree and generally includes temperatures about from −110 to −20 degrees C., preferably about from −55 to −35 degrees C. Typically, the contact is done in the presence of a suitable inert diluent such as, for example, an ether, e.g., diethyl ether, THF, a liquid alkane, e.g., liquid butane, pentanes, hexanes, etc., and mixtures thereof, and so forth and the like. Typically, the alkoxy allene, itself neat, or in a diluent, say, THF, is added slowly to the lithium donating organic agent, itself in an ether, say, THF and/or liquid alkane. Concentrations of the lithium donating organic agent for the contact can range quite broadly to include, say, about from 0.1 to 10M, and preferably about from 1 to 4M. Duration of this step can be from several minutes to several hours as typically follows completion of the addition of the alkoxy allene. This step generally results in formation of a lithium alkoxy allene, nominally a compound represented by the following general formula:

$$Q'_2-C=C=C(Li)OA \tag{X}$$

wherein

Q' is as is defined in the formulae (I) and (VI), and
A is as defined in the formula (VI).

However, this intermediate need not be isolatable to provide practice residing within the spirit of this invention.

The alkoxy allenes can be obtained or prepared by known procedures or by procedures analogous thereto. See e.g., Hoff et al., supra at 916 et seq.

The lithium donating organic agents can be obtained or prepared by known procedures or by procedures analogous thereto. See e.g., Hoff et al., supra at 916 et seq.

At any rate, product from the step involving contact of the alkoxy allene with the lithium donating organic agent is next contacted with the di(inert-substituted)ketone in the second-noted step. The temperature employed is one at which this step can be successfully carried out to any useful degree and generally includes temperatures about from −100 to 20 degrees C., preferably about from −55 to 0 degrees C., with a gradual warming done following initial contact. Typically, the contact is done in the presence of a suitable inert diluent such as that employed in the preceeding step. Typically, the di(inert-substituted)ketone is added slowly, often neat, to the lithium alkoxy allene, itself in diluent from the proceeding step. Duration of this step can be from several minutes to several hours as typically follows completion of the addition of the alkoxy allene. This step generally results in formation of a new alkoxy allene, which may be considered an alkoxide allene, nominally a compound represented by the following general formula:

$$Q_2(O^-)C-C(OA)=C=CHQ' \tag{XI}$$

wherein

Q and Q' are each as in the formulae (I), (III) and (VI), and
A is as in the formula (VI).

However, this intermediate need not be isolatable to provide practice residing within the spirit of this invention. This step may be terminated by quenching, say, with water.

The di(inert-substituted)ketones can be prepared by known procedures or by procedures analogous thereto. As one illustration, a suitable carboxylic acid having inert-substituted moiety thereon can be converted to corresponding acid chloride, say, by reaction of the acid with thionyl chloride. The acid chloride can be reacted with a source of inert-substituted moiety, e.g., an aromatic compound such as benzene, employing a Lewis Acid catalyst such as, for example, aluminum trichloride, to provide the corresponding di(inert-substituted)ketone. Numerous other procedures are known to prepare the di(inert-substituted)ketone as well.

At any rate, product, from the step involving contact of the di(inert-substituted)ketone with the product from the preceeding step, is hydrolyzed under suitable acidic conditions sufficient to not destroy the product (III). The temperature employed is one at which this step can be successfully carried out to any useful degree and generally includes temperatures about from −20 to 50 degrees C., preferably about from 10 to 30 degrees C. A suitable polymerization inhibitor such as, for example, hydroquinone, and so forth and the like, is advantageously added at the beginning of this step. Duration of this step can be about from an hour or so to several days as follows completion of the initial contact. This step may result in the hydrolysis of the alkoxy allene. Nonetheless, this step results in preparation of the alpha-hydroxyl-alpha,alpha-di(inert-substituted) -alpha',beta'-ene ketone.

Said ene ketone can be recovered if desired by known methods. For example, distillation under reduced pressure with cooling of the collected product may be used to advantage in this respect. Said ene ketone is desirably stored under an inert atmosphere at subzero, in terms of degrees C., temperatures.

Yields of said ene ketone can be excellent. As such, yields of at least about 50 percent of theory, at least about 65 percent of theory and even at least about 80 percent of theory, based on the alkoxy allene, presuming that to be the limiting reagent, can be achieved by the practice of the present invention.

The following specifically embodied examples, particularly those numbered, further illustrate the present invention. Parts and percentages therein are by weight unless otherwise specified.

PRELIMINARY PREPARATIONS

In general, cyclobutylphenyl ketone was prepared by forming the acid chloride of cyclobutyl carboxylic acid with thionyl chloride. The acid chloride was then reacted with benzene in the presence of aluminum trichloride to form the desired ketone.

1-Methoxy-1,2-propadiene was prepared generally by the method of Hoff et al., supra at 916 et seq.

1-Methoxy-2-propyne, used to prepare the above-mentioned diene, was prepared generally by the method of Brandsma, supra.

1-(N,N-dimethylamino)-2-propyne, used to prepare acetylenic Grignard reagent, was prepared generally by the method of Verkrysse et al., supra.

The acetylenic Grignard reagent, 1-(N,N-dimethylamino)-2-propyn-3-magnesium chloride, was prepared as follows:

A 10 L roundbottom flask equipped with nitrogen inlet, addition funnel, reflux condenser and mechanical stirrer was charged with magnesium turnings (144 g, 5.9 mol), and 300 mL of THF were added, followed by butyl chloride (40 g, 0.4 mol). The reaction was started by adding a few crystals of iodine and gently heating. After the initial butyl chloride had all reacted, an additional 1.7 L of THF were added, and the remaining butyl chloride (510 g, 5.5 mol) was added at such a rate over the course of about one hour that the reaction mixture was maintained under gentle reflux. The reaction mixture was refluxed for an additional hour. Then 4 L of a mixture of THF containing 1-dimethlyamino-2-propyne (250 g, 3.0 mol) was added over 45 minutes. An additional 300 g of 85 percent dimethyl aminopropyne (255 g, 3.1 mol) was added in about 20 minutes. The reaction was exothermic and remained at the reflux temperature without external heating. After all of the aminopropyne had been added, the reaction was continued at reflux with heating for an additional 2 hours. The acetylenic Grignard resulted. The reaction mixture was allowed to cool to 60 degrees C.

EXAMPLE 1

1-Cyclobutyl-1-hydroxy-1-phenylbut-3-en-2-one was prepared as follows:

A 6-L three-neck flask equipped with mechanical stirrer, nitrogen gas inlet, addition funnel, thermometer and methanol-liquid nitrogen cooling bath was charged with 1 L THF. The THF in the flask was cooled to −40 degrees C., and n-butyllithium (1.0 L, 2.5M in hexane) was added dropwise in about 10 minutes. The reaction mixture was kept under a nitrogen atmosphere until the addition of water (see below). A sample of 1-methoxy allene (175 g, 2.5 mol) was added over a period of 30 minutes while the temperature was maintained at −40 to −50 degrees C. The reaction mixture was stirred for another 0.5 hr. at −40 C. Cyclobutylphenyl ketone (352 g, 2.2 mol) was added dropwise over 45 minutes at a temperature of about −40 degrees C. After addition of this ketone was complete, over the course of one hour the reaction mixture was allowed to warm to −10 degrees C. Water (170 mL) was added dropwise, while maintaining an internal temperature of 0 degrees C. Four grams of hydroquinone were added to the reaction mixture, followed by 500 mL of 20 percent sulfuric acid solution, followed by 600 mL of methanol, while maintaining the temperature at or below 30 degrees C. The hydrolysis of this heterogeneous mixture proceeded slowly and was complete in 40 hrs. The organic mixture was washed with two (2) 1-L portions of water. The aqueous layers were combined and extracted once with 0.5 L hexane. All organic layers were combined and dried over sodium sulfate. The sodium sulfate was removed by filtration, and the solvent was removed from the filtrate by vacuum distillation, using an aspirator as the vacuum source. This yielded a sample of 490 g of crude enone product, which was pure by nuclear magnetic resonance (NMR) spectroscopy, but was further purified by bulb to bulb distillation, using a Kugelrohr apparatus. Prior to vacuum distillation, another 2 g of hydroquinone was added to prevent polymerization.

The 1-cyclobutyl-1-hydroxy-1-phenylbut-3-en-2-one distilled as a light yellow oil at 110–125 degrees C. at 0.1 mm Hg (403 g, 85 percent yield).

EXAMPLE 2

1-Cyclobutyl-7-(N,N-dimethylamino)-1-hydroxy-1-phenylhept-5-yn-2-one, with its hydrochloride salt (ML-1012), was prepared as follows:

Over a period of 30 minutes, a mixture of 1-cyclobutyl-1-hydroxy-1-phenylbut-3-en-2-one (380 g, 1.759 mol) in 500 mL THF was added to the acetylenic Grignard reagent freshly prepared from the foregoing preliminary preparation, 1-(N,N-dimethylamino)-2-propyn-3-magnesium chloride, at 60 degrees C. After an additional hour at 58–65 degrees C., 40 mL water was added dropwise. Most of the THF and excess dimethylaminopropyne by-product were stripped from the product by rotary evaporation employing aspirator pressure and cooling of the receiving flask. The residue which remained was poured onto 1.5 L of an ice/water mixture containing 750 mL concentrated HCl and 1 L toluene. This resulted in the formation of three (3) layers. The lower acidic water layer was separated, and it did not contain any substantial amounts of product. There were two (2) organic layers, which were washed with 2 L of water; the layers were separated, and the aqueous layer was extracted with 0.5 L toluene. The organic layers were discarded. The aqueous layer was made basic using 100 mL of concentrated ammonium hydroxide, and it was extracted with two (2) 375 mL portions of toluene. The combined toluene extracts were made acidic with 1 L of 2.5M hydrochloric acid solution, and the acidic aqueous layer was washed once more with 0.5 L toluene. The acidic aqueous layer was made basic using a 10M sodium hydroxide solution (about 300 mL), and it was extracted twice with a total of 800 mL toluene. The cloudy toluene layers were combined, filtered through celite and dried over sodium sulfate. The sodium sulfate was removed by filtration with a toluene wash, yielding in a toluene solution product 1-cyclobutyl-7-(N,N-dimethylamino)-1-hydroxy-1-phenylhept-5-yn-2-one.

Dry hydrogen chloride gas was passed into the toluene solution until the solution was saturated. Then 250 mL of methyl ethyl ketone (MEK) was added to facilitate crystallization and filtration. The HCl salt of the final product was removed by filtration, and it was washed on the filter with MEK. The product thus obtained weighed 230 g after drying in the vacuum oven at 40 degrees C. This dried product was placed in a 2-L, 3-neck flask equipped with mechanical stirrer and reflux condenser. One liter of a mixture of MEK and isopropyl alcohol (IPA), MEK to IPA ratio of 4:1, was added. The mixture was heated to reflux, and the 230 g of salt dissolved completely. The solution was gravity filtered and the filtrate was allowed to cool to room temperature with stirring while a few seed crystals of the desired HCl salt were added occasionally to aid in smooth crystallization. After a total time of 16 hours, the recrystallized salt was removed by filtration and washed with MEK. The recrystallized salt was dried to consant weight in a vacuum oven at 40 degrees C. to yield 206 g of recrystallized ML-1012 as white crystals. A second crop of HCl salt of the final product was obtained by combining all filtrates, concentrating these, then adding 250 mL MEK and stirring for 16 hours to provide an additional 60 of the same HCl salt product. (Net yield of the two unrecrystallized HCl salt product crops was thus 290 g, about 49 percent of theory based on the enone.) This second crop was also recrystallized to furnish a nearly colorless recrystallized HCl salt second crop (estimated yield, about 90 percent from the 60 g HCl salt second crop product). The recrystallized ML-1012 was essentially pure by NMR spectroscopy.

SYNTHETIC SCHEMES

The following synthetic schemes yet further illustrate the present invention. Synthetic Scheme I illustrates general embodiments within the spirit of this invention, and Synthetic Scheme II illustrates specific embodiments within the spirit of this invention.

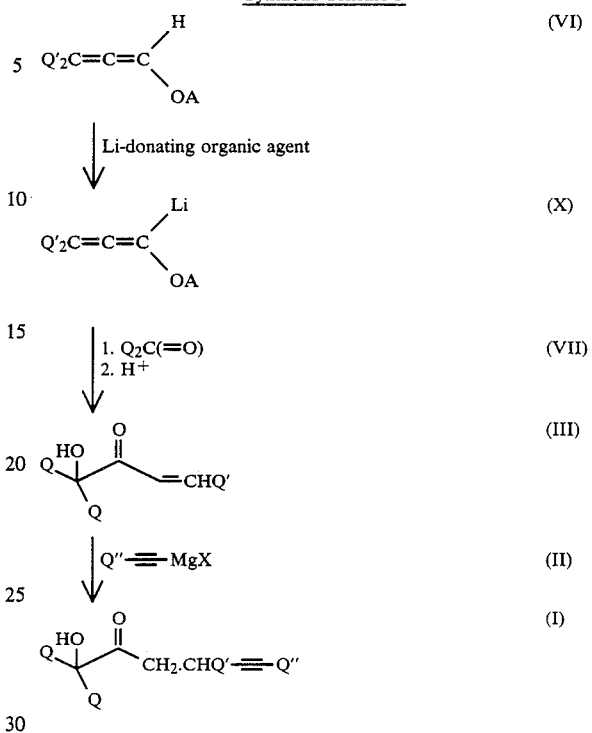

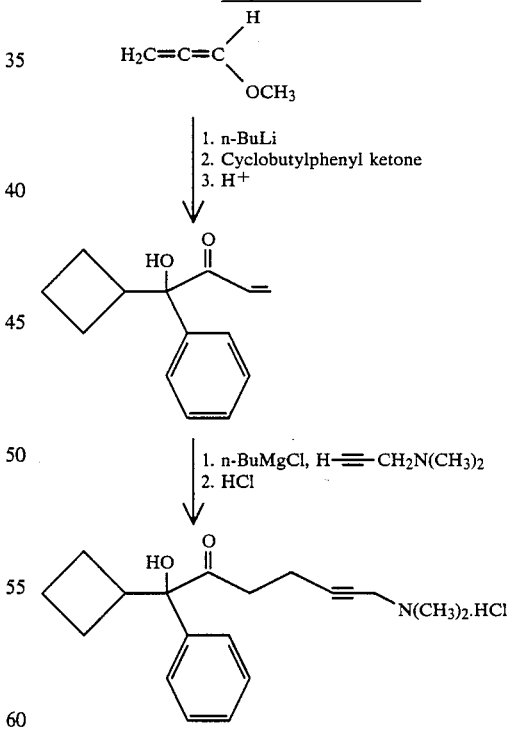

CONCLUSION

The present invention is thus provided. Numerous adaptations and modifications can be effected by those skilled in the art within the spirit of this invention, the scope of which is particularly pointed out by the following distinctly claimed subject matter.

What is claimed is:

1. A procedure for preparing an alpha-hydroxyl alpha,alpha-di(non-heterocyclic inert substituted)-gamma',delta'-yne ketone comprising contacting an acetylenic Grignard reagent with an alpha-hydroxyl-alpha,alpha-di(non-heterocyclic inert substituted)-alpha',beta'-ene ketone outside the presence of an additional complexing agent by step(s) under conditions sufficient to prepare said yne ketone.

2. The procedure of claim 1, which is carried out in a suitable diluent.

3. The procedure of claim 1, wherein said yne ketone is a 1,1-di(non-heterocyclic inert-substituted)-1-hydroxy-7-Aminohept-5-yn-2-one.

4. The procedure of claim 3, wherein the 7-Amino moiety is a tertiary amino moiety.

5. The procedure of claim 3, wherein the 1,1-di(non-heterocyclic inert substituted)-1-hydroxy-7-Aminohept-5-yne-2-one is a compound represented by the following general formula:

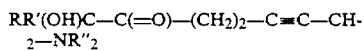

wherein
R is cycloalkyl having three to six carbon atoms, polycycloalkyl of seven to eleven carbon atoms, or substituted or unsubstituted aryl, polycycloaryl or polycycloalkyl;
R' is phenyl or para-fluorophenyl, and
R" is independently at each occurrence hydrogen, alkyl having one to three carbon atoms, or phenylalkyl with its alkyl moiety having one to three carbon atoms, or R"$_2$ is tetramethylene, pentamethylene, or hexamethylene, with
R and R' being considered inert-substituted groups.

6. The procedure of claim 5, wherein
R is phenyl, para-fluorophenyl, cyclobutyl, cyclohexyl or adamantyl, and
R" is independently at each occurrence alkyl having one to three carbon atoms, or phenylalkyl with its alkyl moiety having one to three carbon atoms, or R"$_2$ is tetramethylene, pentamethylene, or hexamethylene.

7. The procedure of claim 6, wherein
R is cyclobutyl;
R' is phenyl, and
R" at each occurence is methyl.

8. The procedure of claim 1, 2, 3, 4, 5, 6 or 7, wherein yield of said yne ketone is at least about 40 percent of theory.

9. The procedure of claim 3, 4, 5, 6 or 7, further comprising contacting said yne ketone with a suitable acid under conditions sufficient to prepare said yne ketone as a salt thereof.

10. The procedure of claim 9, wherein the suitable acid is HCl.

11. The procedure of claim 1, 2, 3, 4, 5, 6 or 7, wherein yield of said yne ketone is at least about 50 percent of theory.

* * * * *